United States Patent [19]

Bach, Jr. et al.

[11] Patent Number: 5,044,375

[45] Date of Patent: Sep. 3, 1991

[54] UNITARY INTRAVASCULAR DEFIBRILLATING CATHETER WITH SEPARATE BIPOLAR SENSING

[75] Inventors: Stanley M. Bach, Jr.; J. Edward Shapland, both of Shoreview; Douglas J. Lang, Arden Hills; Roger W. Dahl, Andover, all of Minn.

[73] Assignee: Cardiac Pacemakers, Inc., St. Paul, Minn.

[21] Appl. No.: 447,908

[22] Filed: Dec. 8, 1989

[51] Int. Cl.$^5$ ............................................. A61N 1/05
[52] U.S. Cl. .............................. 128/786; 128/419 P; 128/642
[58] Field of Search ............... 128/642, 784, 785, 786, 128/419 P

[56] References Cited

U.S. PATENT DOCUMENTS

| | | | |
|---|---|---|---|
| 3,942,536 | 3/1976 | Mirowski et al. | 128/419 D |
| 4,289,144 | 9/1981 | Gilman | 128/785 |
| 4,332,259 | 6/1982 | McCorkle, Jr. | 128/786 |
| 4,355,646 | 10/1982 | Kallok et al. | 128/786 |
| 4,393,883 | 7/1983 | Smyth et al. | 128/785 |
| 4,444,195 | 4/1984 | Gold | 128/786 |
| 4,481,953 | 11/1984 | Gold et al. | 128/419 P |
| 4,559,951 | 12/1985 | Dahl et al. | 128/642 |
| 4,567,900 | 2/1986 | Moore | 128/784 |
| 4,567,901 | 2/1986 | Harris | 128/786 |
| 4,581,953 | 4/1986 | Walston et al. | 74/501 R |
| 4,603,705 | 8/1986 | Speicher et al. | 128/786 |
| 4,614,192 | 9/1986 | Imran et al. | 128/419 D |
| 4,662,377 | 5/1987 | Heilman et al. | 128/419 P |
| 4,819,662 | 4/1989 | Heil, Jr. et al. | 128/419 P |
| 4,856,524 | 8/1989 | Baker, Jr. | 128/419 PG |

FOREIGN PATENT DOCUMENTS 2157954  8/1987  United Kingdom.

OTHER PUBLICATIONS

*Orthogonal Electrogram Sensing*, Bruce N. Goldreyer et al, Pace, vol. 6, pp. 464-469 (Mar.-Apr. 1983, Part III).

*Primary Examiner*—William E. Kamm
*Assistant Examiner*—Scott M. Getzow
*Attorney, Agent, or Firm*—Haugen and Nikolai

[57] ABSTRACT

A cardioversion system includes a bipolar sensing circuit with two sensing electrodes, and a cardioversion circuit with two spaced apart spring electrodes. The sensing electrodes are spaced apart from one another but kept sufficiently close to one another for isolated, localized R-wave sensing. The sensing electrodes further are positioned remotely of the cardioversion electrodes, to avoid post-shock abnormalities which otherwise would interfere with a timely R-wave sensing, to substantially prevent the discharge of an unnecessary cardioversion pulse after return of the heart to normal cardiac rhythm. One preferred version of the system is a unitary catheter including a distal tip electrode and ring electrode as the sensing electrodes, and to substantially larger, more proximal spring electrodes for defibrillation. Alternatively, the defibrillation electrodes and the sensing electrodes can be provided on two separate catheters. Yet another alternative involves providing one or more patch electrodes as defibrillation electrodes.

61 Claims, 4 Drawing Sheets

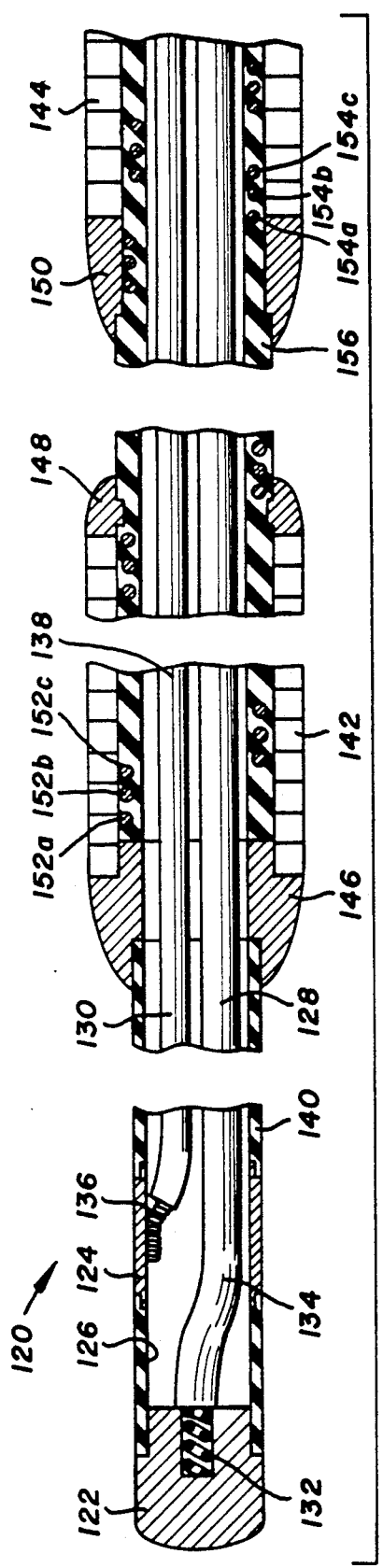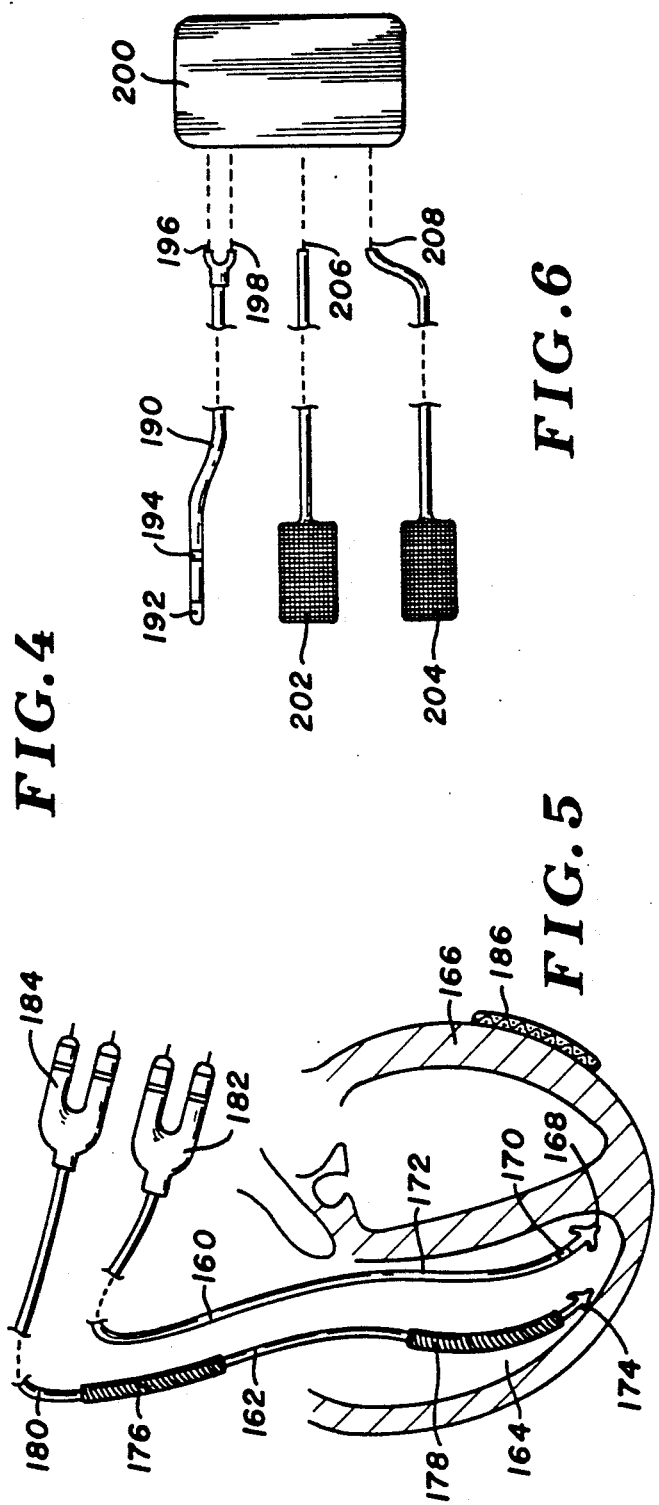
FIG.4
FIG.5
FIG.6

UNITARY INTRAVASCULAR DEFIBRILLATING CATHETER WITH SEPARATE BIPOLAR SENSING

BACKGROUND OF THE INVENTION

This invention relates to body implantable medical devices, and more particularly to defibrillating catheters employing bipolar sensing.

Heart disease is a major cause of deaths in the United States and in other industrial nations. Tachyarrythmias (rapid disturbances in cardiac electrical activity), in particular the conditions of ventricular tachycardia, ventricular flutter and ventricular fibrillation, are widely believed to be the primary cause of sudden deaths associated with heart disease. Atrial tachyarrythmic conditions, on the other hand, are not considered life threatening unless they lead to rapid ventricular disturbance.

Recent experience confirms that tachyarrythmic conditions frequently can be corrected by applying relatively high energy electrical shocks to the heart, a technique often referred to as cardioversion. Cardioversion devices include implantable electronic stand-by defibrillators which, in response to the detection of an abnormally rapid cardiac rhythm, discharge sufficient energy through electrodes connected to the heart to de-polarize and restore the heart to normal cardiac rhythm.

Cardioverting or defibrillation devices typically include means for monitoring heart activity as well as delivery of cardioversion energy. For example, U.S. Pat. No. 3,942,536 (Mirowski et al) discloses an intravascular catheter with a cap electrode at the distal tip, a distal electrode including a plurality of rings near the tip, and a proximal electrode also consisting of a plurality of rings. The tip and distal electrodes are used to provide pacing pulses, while defibrillation pulses are provided using the distal and proximal electrodes. A probe is provided to sense pressure in the right ventricle, to initiate cardioversion upon sensing a pressure that does not exceed a predetermined threshold.

U.S. Pat. No. 4,355,646 (Kallok et al) is directed to a transvenous defibrillating lead with one tip electrode and three additional, annular electrodes. The tip electrode and the most distal of the annular electrodes are placed in the right ventricle and used to measure impedance changes in the ventricle. Defibrillating pulses are delivered across all four of the electrodes.

A key factor in successful defibrillation by implantable devices is the timely and accurate detection of the R-waves, the relatively weak electrical signals produced by ventricular contraction. In particular, the sensing means (one or more electrodes) of the defibrillating device must be capable of quickly detecting abnormally high cardiac rhythm in order to trigger the defibrillation pulse. Perhaps more importantly, the sensing means preferably is able to confirm a successful defibrillation, i.e. a return to normal cardiac rhythm, as soon as possible after each defibrillation pulse. Otherwise, there is the danger of the device delivering an unnecessary and possibly harmful defibrillation pulse.

The advantage of preventing unnecessary or undue defibrillation pulses is recognized in U.S. Pat. No. 4,614,192 (Imran et al). Imran teaches an implantable cardiac defibrillator employing bipolar sensing, in particular a bipolar sensing electrode assembly including a distal tip electrode and a nearby ring electrode, along with two sensing and high voltage delivery electrodes, one in the superior vena cava and another in the form of a patch over the myocardium, near the apex of the heart. This system contemplates three separately implanted electrodes or groups of electrodes. A unitary intravascular multiple electrode catheter is disclosed in U.S. Pat. No. 4,603,705 (Speicher et al). The catheter includes three electrodes: a distal tip electrode, an intermediate spring electrode and a proximal spring electrode. The tip and intermediate electrodes are used in pacing and sensing, while the intermediate and proximal spring electrodes are used to deliver defibrillation pulses.

Use of a common lead for sensing and delivering defibrillation pulses, however, interferes with the timely sensing of R-waves. In particular, tissue proximate the cardioversion discharge electrodes temporarily loses much of its ability to conduct electrical impulses immediately after discharge, resulting in an effective suppression of the R-wave immediately following a defibrillation pulse. Thus, post-shock sensing abnormalities prevent an immediate sensing that the heart has returned to normal sinus rhythm in response to the defibrillation pulse, presenting the risk that another, unneeded defibrillation pulse will be delivered.

Therefore, it is an object of the present invention to provide a unitary intravascular implantable device in which post-defibrillation pulse sensing abnormalities are substantially reduced or eliminated.

Another object is to provide a unitary defibrillation catheter with sensing circuitry independent of the defibrillation circuitry and with increased spacing of sensing electrodes from the nearest defibrillation electrode, for more discrete and localized electrograms.

Another object of the invention is to provide an implantable defibrillation device with a defibrillation pulse delivery system with electrodes and conductors suited for relatively high energy defibrillation, along with independent sensing circuitry including electrodes and conductors suited to sensing.

Yet another object is to provide a unitary defibrillation catheter which simultaneously affords optimum spacing between bipolar sensing electrodes, between a pair of defibrillation electrodes, and between the most adjacent sensing and defibrillation electrodes.

SUMMARY OF THE INVENTION

To achieve these and other objects, there is provided a unitary intravascular cardioversion device. The device includes an elongate, flexible and dielectric catheter body having a proximal end region, a distal end region and a lumen means formed in the body from the proximal end region to the distal end region. The device has a cardioversion circuit including a cardioversion electrode means mounted on the catheter body proximally of the distal region, and a flexible conductor means connected to the cardioversion electrode means, for conducting electrical pulses between the cardioversion electrode means and the proximal end region, and a cardioversion connector means near the proximal end region for electrically coupling the conductor means with a cardioversion pulse generating means, thereby to deliver cardioversion pulses to the cardioversion electrode means. The device further includes a cardiac sensing circuit including a first sensing electrode mounted on the catheter body at the distal end region, a first sensing conductor means connected to the first sensing electrode for detecting electrical pulses between the first sensing electrode and the proximal end region, a second sensing electrode mounted on the catheter body at the distal end region proximally of the first sensing electrode and spaced apart from the first sensing electrode by a predetermined first distance, a second flexible sensing conductor means connected to the second sensing electrode for detecting electrical pulses between the second sensing electrode and the proximal end region, and a sensing connector means near the proximal end region for electrically coupling the first and second sensing conductor means with a pulse sensing means, thereby to utilize the first and second sensing electrodes as a bipolar pulse sensing pair independent of the cardioversion circuit.

Preferably, the first sensing electrode is a distal tip electrode at the distal end of the catheter body, and the second sensing electrode is a ring electrode surrounding the catheter body and spaced apart from the tip electrode a distance in the range of from one to twenty millimeters, preferably ten millimeters.

The cardioversion means advantageously includes distal and proximal cardioversion electrodes in the form of flexible, electrically conductive coils. In this event, the conductor means includes a first cardioversion conductor coupled to the distal conversion electrode and a second cardioversion conductor coupled to the proximal electrode. Both cardioversion conductors are flexible and contained in the lumen means, with the cardioversion connector means then coupling both cardioversion conductors to the pulse generating means. Each of the proximal and distal cardioversion coils can have a length in the range of from 1 to 7.5 centimeters.

The preferred spacing between the proximal sensing electrode or ring electrode, and the distal defibrillating electrode, is at least one centimeter. This ensures that heart tissue proximate and between the sensing electrodes is effectively isolated from the tissue subject to the defibrillation pulse. As a result the device affords accurate R-wave sensing immediately after applying a defibrillation pulse, substantially eliminating the possibility of charging for and delivering unnecessary defibrillation pulses after the heart has returned to normal sinus rhythm.

A further advantage of the present invention is that it permits selection of the distance between the defibrillating electrodes for a preferred positioning of the distal defibrillating electrode, e.g. in the right ventricle near the apex, and of the proximal defibrillating electrode, e.g. high in the right atrium or within the superior vena cava. Total electrical independence of the sensing system from the defibrillation circuit permits simultaneous optimum separation of the tip and ring electrodes, the ring electrode and distal defibrillating electrode, and the two defibrillating electrodes, an advantage not attainable when a single electrode is utilized for defibrillation pulsing and sensing. A further advantage of the present invention resides in the ability to tailor electrodes and conductors specifically for the sensing system, and to tailor other electrodes and conductors specifically for the defibrillation circuit. The relatively high currents and voltages involved in the defibrillation circuit require relatively large surface area electrodes to reduce impedance, and conductors formed of drawn brazed strand (DBS) wires or other highly conductive material. The sensing system does not impose these requirements. A unitary catheter with independent sensing and cardioversion systems, in accordance with the present invention, permits a better impedance matching of the two sensing electrodes. Such catheter further allows selection of materials and component sizes customized to either sensing or cardioversion, for example multi-conductor tube (MCT) construction involving coaxial windings for defibrillation conductors, in combination with sensing conductors contained within a central lumen of the catheter.

Another aspect of the present invention is a cardioversion and sensing system in which sensing electrodes are mounted on a sensing catheter for use in conjunction with a pair of cardioversion electrodes. The cardioversion electrodes may be provided as coils on a separate cardioversion catheter, as two separate patch electrodes, or as a single defibrillation coil in combination with a patch electrode. The electrodes are placed in the region of the heart, encompassing ventricular and atrial endocardial placement, intraparacardial or extraparacardial placement, vascular positioning, and in general within the thoracic cavity. The use of patch electrodes for cardioversion, alone or with a coil electrode, affords a high degree of flexibility in electrode positioning.

Thus, in accordance with the present invention, a catheter system provides sensing electrodes in complete isolation from a defibrillation pulse delivery system, for substantially immediate R-wave sensing following the application of each defibrillation pulse.

IN THE DRAWINGS

For a further understanding of the above and other features and advantages, reference is made to the following detailed description and the drawings, in which:

FIG. 4 is a sectional view of a portion of an alternative embodiment catheter constructed in accordance with the present invention;

FIG. 5 is a plan view of another alternative embodiment of the invention comprising two leads separately implanted in the heart; and FIG. 6 is a schematic view of yet another alternative embodiment using patch electrodes for defibrillation.

DETAILED DESCRIPTION OF THE PREFERRED EMBODIMENT

Figure 1:
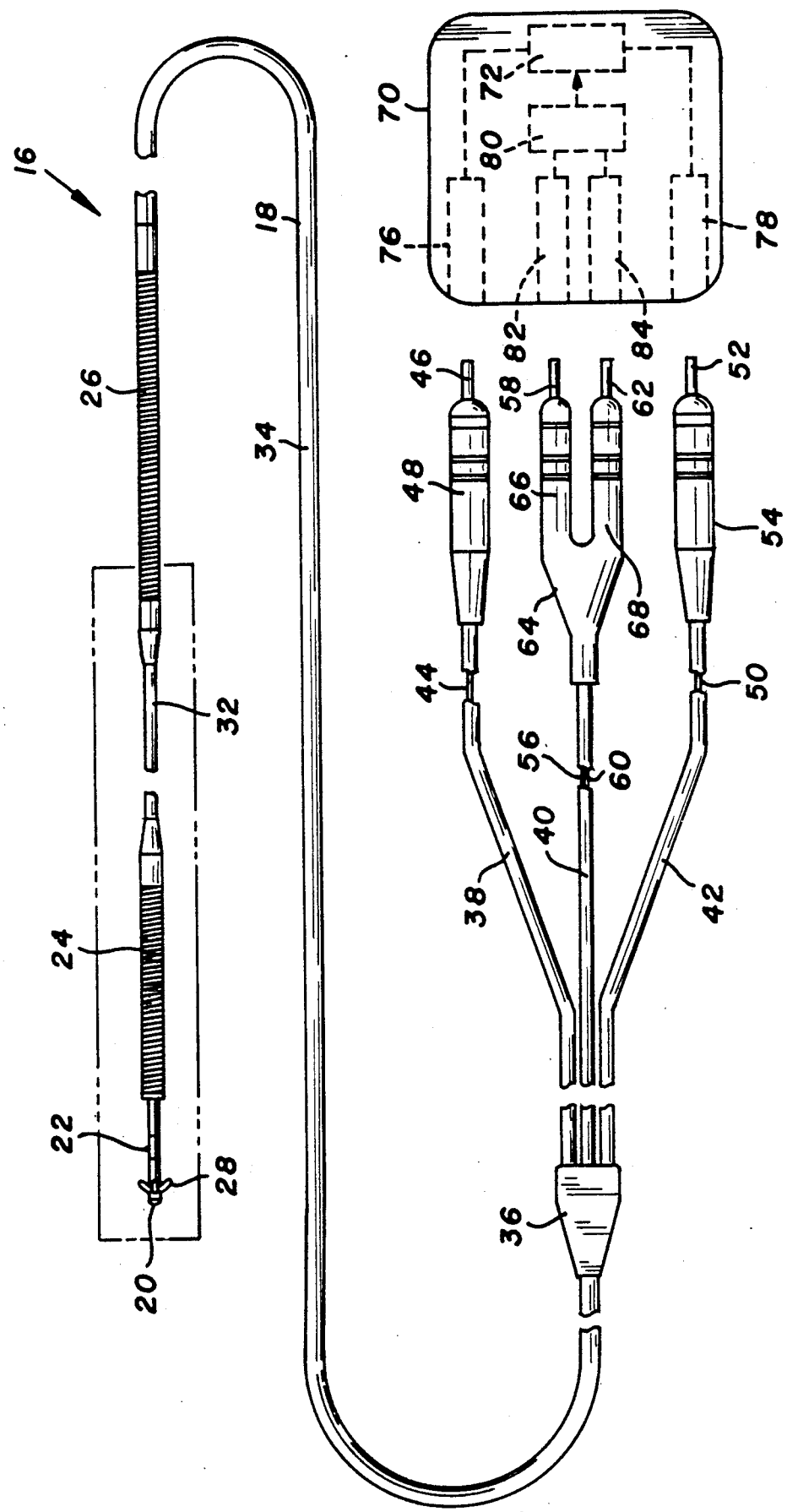
FIG. 1 is a plan view of a unitary intravascular defibrillating catheter constructed in accordance with the present invention.

Turning now to the drawings, there is shown in FIG. 1 a unitary intravascular defibrillation catheter 16 including an elongate and flexible catheter body 18 constructed of a dielectric material, for example silastic or polyurethane. Four electrodes are mounted to the catheter body, including a distal tip electrode 20 at the distal end of the body, a bipolar ring electrode 22, a distal spring electrode 24 and a proximal spring electrode 26. A plurality of tines 28 near the distal end of the catheter, formed of the dielectric material comprising the body, assist in the positioning and securing of the catheter during implant.

Catheter body 18 further includes a reduced diameter distal tubing portion which supports the tip and ring electrodes, a proximal reduced diameter tubing portion 32 between spring electrodes 24 and 26, and a sheath portion 34 encompassing the majority of the catheter length.

A reinforcing member 36 provides a junction for sheath 34 and three lengths of electrically insulative tubing 38, 40 and 42. Tubing 38 contains a conductor 44 provided for transmitting electrical signals from distal spring electrode 24 to a pin 46. An electrically insulative boot 48 surrounds pin 46 and tubing 44. A conductor 50, contained within insulative tubing 42 and sheath 34, electrically couples proximal spring electrode 26 and a pin 52, with pin 52 and tubing 42 being surrounded by an electrically insulative boot 54.

Similarly, a conductor 56 electrically couples ring electrode 22 with a pin 58, and a conductor 60 similarly couples tip electrode 20 with a pin 62. Pins 58 and 62 and conductors 56 and 60 are surrounded by an insulative plug 64 with boot portions 66 and 68.

In use, catheter 16, particularly at plug 64 and boots 48 and 54, is electrically and mechanically coupled to a defibrillation control unit 70 including defibrillation pulse generating circuitry 72, represented schematically in FIG. 1. Unit 70 includes a pair of receptacles 76 and 78 for receiving pin 46 and boot 48, and pin 52 and boot 54, respectively, thus to electrically couple spring electrodes 24 and 26 with defibrillation pulse generating circuitry 72. Boots 48 and 54 which the conductors are contained and thus isolated from bodily fluids.

Figure 3:
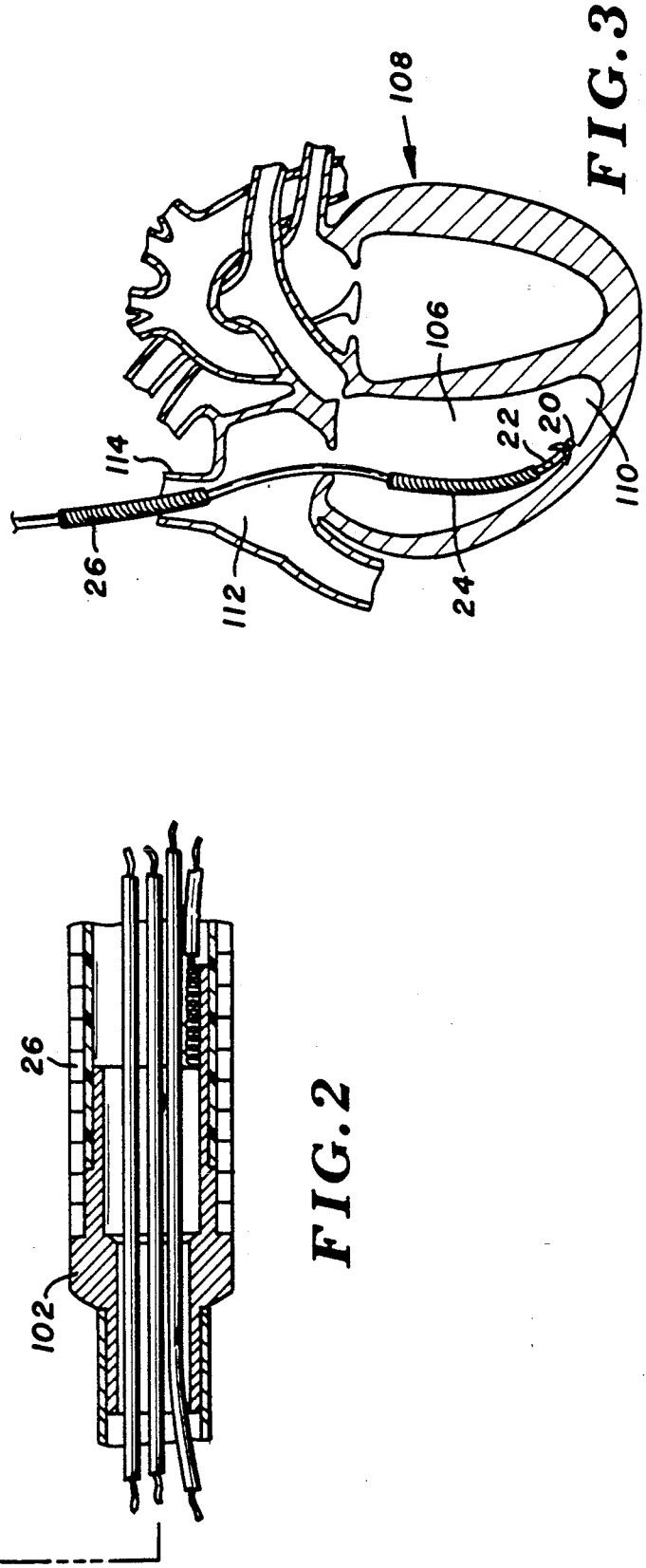
FIG. 3 is a sectional view illustrating the positioning of the catheter of FIG. 1 within the heart.

Catheter 16 is inserted intravenously, for example into the subclavian vein or the cephalic vein, and progressively moved toward the heart until the distal end reaches a selected cardiac chamber. As illustrated in FIG. 3, catheter 16 preferably is inserted to position distal tip electrode 20 and ring electrode 22 in a right ventricle 106 of the heart 108, near the apex 110. Within the ranges for spacing and lengths discussed above, spring electrode 24 preferably is within the right ventricle when tip electrode 20 is positioned as described, with proximal spring electrode 26 located high in the right atrium 112 or in the superior vena cava 114.

With the distal tip positioned as shown, the lead proximal end, still outside the body, is maneuvered to implant the distal tip into the endocardium. Once implanted, distal tip electrode 20, ring electrode 22, conductors 56 and 60 and sensing circuitry 80, cooperate to monitor electrical activity in the heart, in particular R-wave activity.

FIG. 4 shows an alternative design catheter 120 with a solid platinum or titanium tip electrode 122 and an annular electrode 124 near the tip electrode for bipolar R-wave sensing. A central lumen 126 cf catheter 120 contains a pair of conductors 128 and 130 connected to tip electrode 122 and annular electrode 124, respectively. Conductor 128 includes a conductive single coil winding 132 surrounded by an insulative sheath 134 and exposed at its distal end for connection to the tip electrode. Similarly, conductor 130 includes a coil winding 136 surrounded by an insulative sheath 138 and exposed for its connection to the annular electrode. Electrodes 122 and 124 are mounted on a fit tightly within their respective receptacles to provide a positive fluid seal.

Defibrillation unit 70 further includes pulse or heart rate sensing circuitry represented schematically at 80. A pair of sensing receptacles 82 and 84 receive plug 64, to electrically couple distal tip electrode 20 and ring electrode 22 with the sensing circuitry, with the boot portions of the plug member again providing a fluid seal. Further details of defibrillation control unit 70 are not discussed herein as they are known in the art and not particularly germane to the present invention. In short, the connection of pins 46, 52, 58 and 62 as described creates two independent electrical circuits a sensing circuit including tip electrode 20 and ring electrode 22, and a defibrillation circuit including spring electrodes 24 and 26. The sensing circuit monitors heart electrical activity, in particular to sense tachyarrythmias. In response to such sensing, the pulse generating circuit delivers a defibrillating pulse to the heart across spring electrodes 24 and 26.

Figure 2:
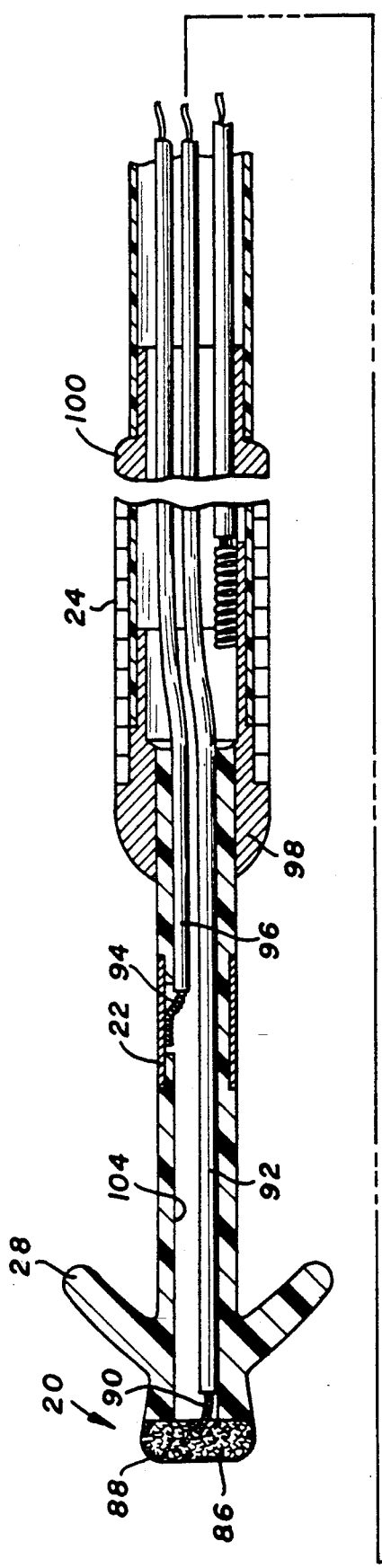
FIG. 2 is a sectional view of a portion of the catheter of FIG. 1.

As seen in FIG. 2, tip electrode 20 is constructed of one or more filaments, preferably a thin wire 86 of platinum or a platinum iridium alloy. The wire is stretched, then crumpled and packed against the distal end of catheter body 18. A screen 88, also of platinum or a platinum alloy, is fastened to the periphery of the catheter body distal end and maintains the crumpled wire in place. For further information regarding this type of electrode, reference is made to U.S. Pat. No. 4,156,429 (Amundson). So constructed, electrode 20 is highly porous, for example consisting of approximately twenty percent platinum alloy by volume, the remaining eighty percent being open to permit passage of bodily fluids through the tip electrode and to admit ingrowth of tissue, which ssists in anchoring the tip electrode after implant. Tip electrode performance may be further enhanced by surface treatment to micro texturize the tip, as disclosed in U.S. Pat. application Ser. No. 325,764 filed Mar. 20, 1989 and assigned to the assignee of this application. This treatment substantially increases the reactive surface area of the tip.

Conductor 60 includes a single wound coil 90 formed of a nickel alloy or other electrically conductive material permitting flexure. The exposed distal end of coil 90 is electrically and mechanically coupled to distal tip electrode 20. The remainder of the coil is surrounded by a flexible, dielectric sheath 92. The remaining conductors are similarly constructed. Conductor 56 includes a single wound coil 94 surrounded by a sheath 96 and with its exposed distal end coupled to ring electrode 22. The ring electrode is constructed of platinum, a platinum iridium alloy or other appropriate electrically conductive and body compatible material. The outer surface area of the ring electrode exposed to bodily tissue and fluids is in the range of from ten to fifty square millimeters, and more preferably is about the same in effective surface area as the tip. If desired, ring electrode 22 car be subject to sputtering or other surface treatment to impart microporosity. For accurate R-wave sensing, ring electrode 22 must be spaced apart from tip electrode 20 in the range of from one to twenty millimeters, with a particularly preferred spacing between these electrodes being about ten millimeters.

Proximally of ring electrode 22 is a fitting 98 which surrounds distal tubing portion 30. Fitting 98 is joined to the distal end of spring electrode 24, and cooperates with a fitting 100 at the proximal end of spring electrode 24 to support the electrode. Distal spring electrode 24 can have a length of from 1 to 7.5 centimeters, and up to 15 centimeters if especially smooth. Preferably electrode 24 is 6 centimeters long, to provide a relatively large exposed surface area necessary for effective delivery of defibrillation pulses. Spring electrode 24 is spaced apart from ring electrode 22 a distance in the range of five to twenty millimeters, although generally a spacing of at least one centimeter is recommended to ensure that heart tissue used in sensing pulse rate, particularly tissue near ring electrode 22, is sufficiently distant from tissue affected by the defibrillation pulse to ensure a localized, isolated and therefore more accurate R-wave sensing.

Proximally of spring electrode 24, a pair of fittings, one of which is shown at 102, support proximal spring electrode 26. Like spring electrode 24, spring electrode 26 is constructed of an electrically conductive and bodily compatible material such as titanium or platinum. Proximal spring electrode 26 can have a length in the range of 1 to 7.5 centimeters, and is preferably 3.8 centimeters long. The spacing between proximal and distal spring electrodes 24 and 26 preferably is about eleven centimeters, although a spacing of from six to fourteen centimeters has been found satisfactory.

Tubing sections 30 and 32, spring electrodes 24 and 26 and sheath 34 cooperate to define a central lumen 104 running the length of the catheter from the distal tip to reinforcing member 36. Conductors 44, 50, 56 and 60 all are contained within lumen 104. Proximally of reinforcing member 36, each of the conductors is contained within its corresponding one of tubing sections 38, 40 and 42. Thus, the proximal tubing sections sheath, spring electrodes, and distal tubing sections form a lumen means in dielectric and flexible distal tubing section 140 of catheter 120.

Defibrillation pulses are applied through a pair of spring electrodes, a distal spring electrode 142 and a proximal spring electrode 144. The distal spring electrode is supported between a pair of fittings 146 and 148 at its opposite ends. Spring electrode 144 is similarly supported between a pair of fittings, one of which is shown at 150.

For transmission of cardioversion pulses between spring electrodes 142 and 144, multi-filament conductors 152 and 154 are connected to electrodes 122 and 124, respectively, and also are electrically coupled to a pulse generator, not shown. Each of conductors 152 and 154 includes a plurality of individual electrically conductive filaments arranged in parallel, helical paths about the center of catheter 120. More particularly, conductor 152 includes filaments 152a, 152b and 152c, embedded in a length of insulative tubing 156 and thus electrically isolated from one another. At their distal ends, however, filaments 152a-c are exposed for electrical coupling to distal spring electrode 142.

Similarly, conductor 154 includes filaments 154a, 154b and 154c. Through the majority of the length of conductor 154, the filaments are embedded in tubing 156 and thus are electrically isolated. The distal ends of the filaments are exposed near electrically conductive fitting 150, for electrical coupling to this fitting, illustrated as an alternative to a coupling of these filaments to spring electrode 144. Conductors 152 and 154 are laterally offset from one another over the entire length of tubing 156 and thus are electrically isolated from one another. The multi-filament construction of these conductors affords the desired flexibility in catheter 120 and the increased cross-sectional conductive area desired for handling high energy cardioversion pulses, while permitting the catheter diameter to remain relatively small. For a further explanation of the helically wound and isolated filament technique, reference is made to U.S. Pat. No. 4,559,951 (Dahl et al).

FIG. 5 discloses yet another approach to separate sensing and defibrillating, employing a sensing catheter 160 and a defibrillation catheter 162, separately implantable within the right ventricle 164 of the heart 166. Sensing catheter 160 includes a tip electrode 168 and a ring electrode 170 near the distal tip but separated from the tube electrode by one to ten millimeters as previously explained. A pair of conductors, contained within insulative tubing 172, connect tip and ring electrodes 168 and 170 with pulse sensing circuitry near the proximal end of sensing catheter 160. Defibrillation catheter 162 includes a distal tip with tines 174 to assist in positioning the catheter upon implant. Proximal and distal spring electrodes 176 and 178 are mounted to catheter tubing 180 as explained in connection with FIGS. 2 and 4. A pair of conductors, one associated with each of spring electrodes 176 and 178, transmit defibrillation pulses to the spring electrodes. The conductors may be contained in a central lumen of the catheter, or alternatively helically wound as explained in connection with FIG. 4. The sensing and defibrillating conductors are coupled to pulse generating and heart rate sensing circuitry by plugs 184 and 182, respectively. If desired, a patch electrode 186, at least equal to spring electrodes 176 and 178 in surface area, is secured to myocardial tissue and used in combination with the spring electrodes or in lieu of one of the spring electrodes. As compared to the embodiments in FIGS. 2 and 4, the two-catheter system in FIG. 5 of course requires a greater degree of skill and effort for implantation. On the other hand, it affords the added advantage of lateral or transverse orientation of the sensing electrodes from the defibrillation spring electrodes, to assure localized R-wave sensing remote from tissue subject to defibrillation, and further to permit optimum positioning of the sensing system and the defibrillation system, each fully independently of the other.

FIG. 6 schematically illustrates a system employing a sensing catheter 190 having a tip electrode 192 and a ring electrode 194 spaced apart from the tip electrode by one to ten millimeters. A pair of conductors in the catheter are connected at their distal ends to electrodes 192 and 194, respectively, and at their proximal ends to pins 196 and 198. The pins are plugged into a defibrillation control unit 200 similar to unit 70 described in connection with FIG. 1, to electrically couple the sensing electrodes to sensing circuitry in the control unit.

The system further includes a pair of defibrillation electrodes in the form of patch electrodes 202 and 204, each of which is subcutaneously implanted in the thoracic region, e.g. secured to myocardial tissue. A conductor electrically couples patch electrode 202 with a proximal pin 206, and another conductor likewise couples patch electrode 204 to a proximal terminal pin 208. Pins 206 and 208 are plugged into control unit 200 to electrically couple the patch electrodes with a pulse generating circuit contained in the control unit.

In this system, catheter 190 is provided solely for sensing and defibrillation is accomplished solely through the patch electrodes. Accordingly, this system is particularly useful in applications calling for maximum flexibility in the positioning of defibrillation electrodes, and in which a single catheter is preferred.

Figure 7:
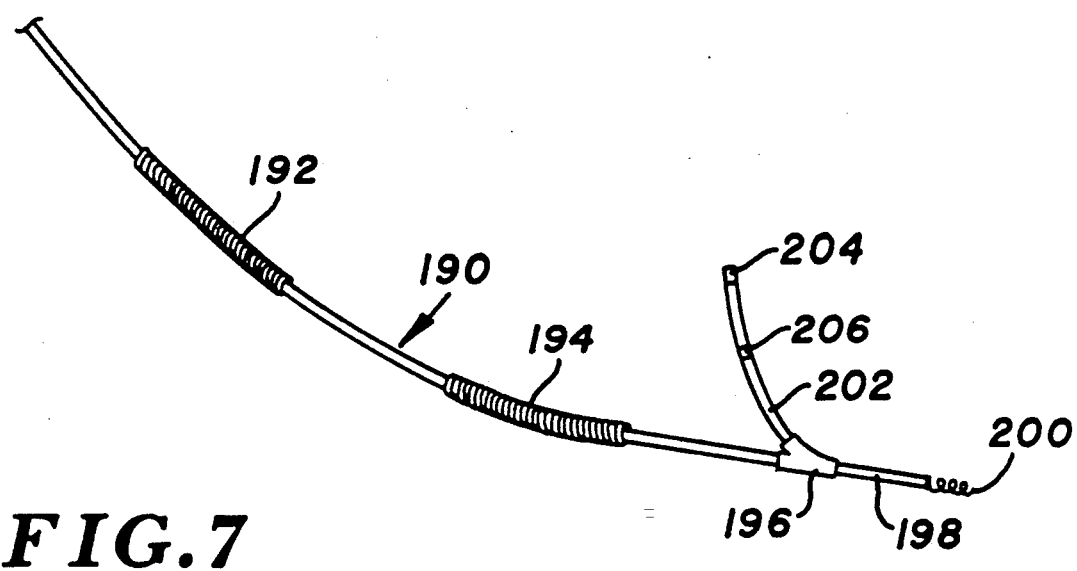
FIGS. 7 and 8 show an alternative embodiment utilizing a bifurcated catheter.
Figure 8:
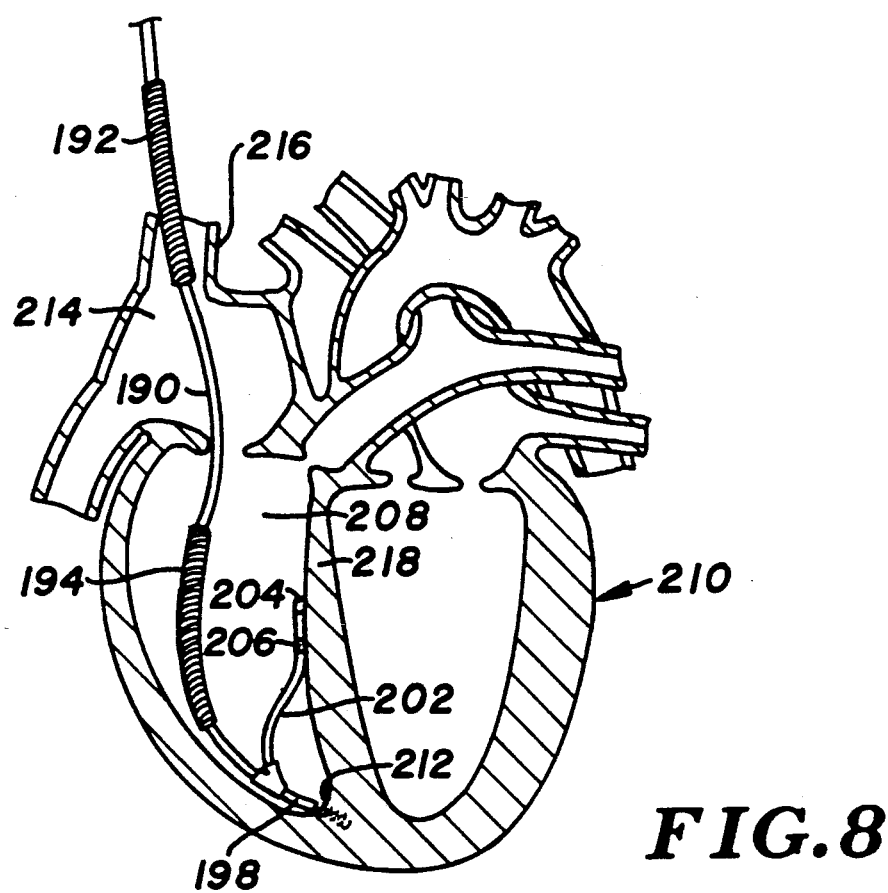

FIGS. 7 and 8 illustrate another alternative, namely a bifurcated catheter 190 having a proximal spring cardioversion electrode 192 and a distal spring cardioversion electrode 194. Separate conductors are connected to spring electrodes 192 and 94 respectively, for transmitting cardioversion pulses between these electrodes. Near the distal end of catheter 190, an insulative boot forms a junction 196. A first extension 198, distally of the junction, supports a helical coil 200 used in a known manner to secure extension 198, and thus the remainder of the lead, to endocardial tissue.

A second extension 202 of the catheter is directed generally proximally of junction 196 but inclined relative to the remainder of the catheter. Two sensing electrodes including a tip electrode 204 and a ring electrode 206, are supported on extension 202 and constructed as previously described. Separate conductors are connected to tip electrode 204 and ring electrode 206 respectively, each for transmitting electrical pulses between its associated sensing electrode and the proximal end region of catheter 190.

As seen in FIG. 8, catheter 190 preferably is inserted to position the distal tip of extension 198 in the right ventricle 208 of the heart 210, at the apex 212. Coil 200 is secured to endocardial tissue at the apex and thus maintains catheter 190 in the desired position. As noted previously in connection with other embodiments, distal spring electrode 194 preferably is within the right ventricle and proximal spring vena cava 216.

Extension 202 of the catheter is inclined away from the remainder of catheter 190 toward the septum 218, preferably to position tip electrode 204 and ring electrode 206 against the septum along the outflow tract, again resulting in sensing remotely of the area subject to cardioversion pulses. In view of the reverse bend in the conductors from the sensing electrodes at junction 196, it is recommended that these conductors be coils, with a known reverse winding technique used to negotiate the relatively sharp bend. In other respects, the electrodes and conductors can be constructed as previously described.

Thus, in accordance with the present invention the R-wave sensing system is configured in complete electrical isolation from the cardioversion system, with a bipolar sensing electrode means interacting with endocardial tissue remote from tissue subject to the immediate electrical affects of cardioversion. Consequently post-shock sensing abnormalities encountered in connection with previous devices, particularly unitary catheters, are substantially eliminated. A more timely and accurate R-wave sensing is achieved, to substantially reduce the risk of generating unnecessary and possibly harmful cardioversion pulses after a return to normal sinus rhythm.

What is claimed is:

1. A unitary intravascular cardioversion device including:
    an elongate, flexible and dielectric catheter body having a proximal end region and a distal end region;
    a cardioversion circuit including a first cardioversion electrode mounted on said catheter body along said distal end region; a first flexible conductor means connected to said first cardioversion electrode for conducting electrical pulses between said first cardioversion electrode and said proximal end region; a second cardioversion electrode mounted on said catheter body proximally of said first cardioversion electrode, spaced apart from said first cardioversion electrode; a second flexible conductor means connected to said second cardioversion electrode for transmitting electrical pulse between said second cardioversion electrode and said proximal end region; and a cardioversion connector means near said proximal end region for electrically coupling said first and second conductor means with a cardioversion pulse generating means, thereby to utilize said first and second cardioversion electrodes as a cardioversion electrode pair; and
    a cardiac sensing circuit electrically isolated from the cardioversion circuit and including a first sensing electrode mounted on said catheter body along said distal end region; a third flexible conductor means connected to said first sensing electrode for transmitting electrical pulses between said first sensing electrode and said proximal end region; a second sensing electrode, mounted on said catheter body along said distal end region proximally of said first sensing electrode and spaced apart from said first sensing electrode by a predetermined first distance; a fourth flexible conductor means connected to said second sensing electrode for transmitting electrical pulses between said second sensing electrode and said proximal end region; and a sensing connector means near said proximal end region for electrically coupling said third and fourth conductor means with a pulse sensing means; wherein each of said first and second cardioversion electrodes has a surface area at least three times the surface area of each of the first and second sensing electrodes, and the sensing electrodes are separated from each of the cardioversion electrodes by a distance sufficient to isolate tissue proximate and between the cardioversion electrodes from tissue adjacent to said sensing electrodes.

2. The cardioversion device of claim 1 wherein:
    said first sensing electrode and said second sensing electrode are mounted on said catheter body distally of said first cardioversion electrode.

3. The cardioversion device of claim 2 further including:
    a lumen means formed in said catheter body from said proximal end region to said distal end region.

4. The cardioversion device of claim 3 wherein:
    said first sensing electrode is mounted at the distal end of said catheter body and comprises a distal tip electrode.

5. The cardioversion device of claim 4 wherein:
    said tip electrode includes a platinum alloy wire, and a platinum alloy screen secured with respect to the distal end of said catheter body, for maintaining the wire crumpled and packed against the catheter body.

6. The cardioversion device of claim 5 wherein:
    said distal tip electrode is microtexturized.

7. The cardioversion device of claim 4 wherein:
    said second sensing electrode comprises a ring electrode about said catheter body and having an outer exposed surface area in the range of from ten to fifty square millimeters.

8. The cardioversion device of claim 7 wherein:
    said first distance is within the range of from one to twenty millimeters.

9. The cardioversion device of claim 8 wherein:
    said first distance is approximately 5 millimeters.

10. The cardioversion device of claim 7 wherein:
    said first and second cardioversion electrodes respectively comprise distal and proximal electrically conductive coils.

11. The cardioversion device of claim 10 wherein:
    each of said proximal and distal coils has a length in the range of from 1 to 7.5 centimeters.

12. The cardioversion device of claim 10 wherein:

said distal coil and said ring electrode are separated from one another by a distance in the range of from five to twenty millimeters.

13. The cardioversion device of claim 12 wherein:
The distance between said ring electrode and distal coil is approximately one centimeter.

14. The cardioversion device of claim 3 wherein:
each of said first, second, third and fourth conductor means comprises an electrically conductive coil winding housed in a dielectric sheath.

15. The cardioversion device of claim 14 wherein:
said lumen means includes a single lumen centrally of said catheter body.

16. The cardioversion device of claim 15 wherein:
said first, second, third and fourth flexible conductor means are contained within said central lumen.

17. The cardioversion device of claim 15 wherein:
said third and fourth flexible conductor means are contained within said central lumen, and said first and second flexible conductor means comprise a plurality of filaments embedded in said catheter body.

18. The unitary intravascular device of claim 1 wherein:
said catheter body is bifurcated to form first and second extensions, said first extension includes a fixation means for securing the catheter body to endocardial tissue, and the first and second sensing electrodes are mounted on said second extension.

19. The unitary intravascular device of claim 18 wherein:
said first and second cardioversion electrodes are disposed proximally of a junction of the first and second extensions.

20. The unitary intravascular device of claim 1 wherein:
said first and second sensing electrodes are substantially equal to one another in surface area, and said first and second cardioversion electrodes are substantially equal to one another in surface area.

21. A defibrillator catheter comprising:
an elongate catheter body comprised of a flexible and dielectric material, and having a proximal end and a distal end;
a distal tip sensing electrode mounted to said catheter at said distal end;
an annular sensing electrode mounted about said catheter body at a selected first distance proximately of said distal tap electrode;
a first defibrillating electrode mounted to said catheter body at a selected second distance proximally of said annular sensing electrode, and a second defibrillating electrode mounted proximally of said first defibrillating electrode and spaced apart from said first defibrillating electrode, each of the defibrillating electrodes having a surface area at least three times the surface area of each of the distal tip sensing electrode and the annular sensing electrode;
first, second, third and fourth conductor means connected respectively to said distal tip electrode, annular sensing electrode, first defibrillating electrode and second defibrillating electrode, said conductor means electrically isolated from one another;
a defibrillator connector means for electrically coupling said third and fourth conductor means to a defibrillation pulse-generating means to form a defibrillation circuit which further includes said defibrillation electrodes; and
a sensing connector means for electrically coupling said first and second conductor means with cardiac sensing circuitry from a bipolar pulse sensing circuit independent of said defibrillating circuit.

22. The defibrillator catheter of claim 21 wherein:
said first distance is in the range of from one to twenty millimeters.

23. The catheter of claim 22 wherein:
said first distance is approximately ten millimeters.

24. The catheter of claim 21 wherein:
each of said first and second defibrillation electrodes is an electrically conductive coil having a length in the range of from 1 to 7.5 centimeters.

25. The catheter of claim 24 wherein:
said second distance is within the range of from five to twenty millimeters.

26. The catheter of claim 25 wherein:
said second distance is approximately one centimeter.

27. The catheter of claim 21 wherein:
said catheter body is insertable into a right ventricle of a heart by way of a superior vena cava, and said second distance and the separation between said first and second defibrillating electrodes are selected to position said second defibrillating electrode within the superior vena cava when said tip electrode is at the apex of the right ventricle.

28. The defibrillator catheter of claim 21 further including:
a lumen means formed in said catheter body from said proximal end to said distal end.

29. The catheter of claim 28 wherein:
each of said first, second, third and fourth conductor means comprises an electrically conductive coil winding housed in a dielectric sheath.

30. The catheter of claim 29 wherein:
said lumen means includes a single lumen centrally of said catheter body.

31. The catheter of claim 30 wherein:
said first, second, third and fourth flexible conductor means are contained within said central lumen.

32. The catheter of claim 30 wherein:
said third and fourth flexible conductor means comprise a plurality of filaments embedded in said catheter body, and said first and second flexible conductor means are contained within said central lumen.

33. The catheter of claim 21 wherein:
said distal tip sensing electrode includes a platinum alloy wire, and a platinum alloy screen secured with respect to the distal end of the catheter body, for maintaining the wire crumpled and packed against the catheter body.

34. The catheter of claim 33 wherein:
said distal tip electrode is microtexturized.

35. The catheter of claim 21 wherein:
said annular sensing electrode has an outer exposed surface area in the range of from ten to fifty square millimeters.

36. The catheter of claim 21 wherein:
said first and second defibrillating electrodes respectively comprise distal and proximal electrically conductive coils.

37. The catheter of claim 21 wherein:
said catheter body is bifurcated to form first and second extensions, with said first extension including a fixation means for securing the catheter body to endocardial tissue.

38. The catheter of claim 37 wherein:
said first and second defibrillating electrodes are disposed proximally of a junction of the first and second extensions.

39. The catheter of claim 21 wherein:
said first and second defibrillating electrodes are substantially equal to one another in surface area.

40. A transvenous defibrillating catheter, insertable into a right ventricle of a heart by way of a superior vena cava, comprising:
an elongate catheter body comprised of a flexible and dielectric material and having a proximal end, a distal end and a lumen means running substantially the length of the catheter body from the proximal end to said distal end;
a distal sensing electrode mounted to said catheter at least proximate said distal end, and an annular sensing electrode mounted to said catheter body a selected first distance proximally of said distal sensing electrode;
a defibrillating electrode means mounted to said catheter body at a selected second distance proximally of said annular sensing electrode and having a surface area at least three times the combined surface areas of the distal sensing electrode and the annular sensing electrode, and a defibrillator conductor means electrically coupled to said defibrillating electrode means for transmitting cardioversion pulses between said defibrillating electrode means and a defibrillation pulse generating means near said proximal end of said catheter body;
a first sensing conductor connected to said distal sensing electrode, and a second sensing conductor connected to said annular sensing electrode, for transmitting electrical signals between said proximal end of the catheter body and said distal sensing electrode and annular sensing electrode, respectively, said sensing conductors being electrically isolated from one another and from said defibrillator conductor means; and
a sensing connector means for electrically coupling said first and second sensing conductors with a cardiac sensing circuit to form a bipolar pulse sensing means independent of said defibrillating means.

41. The transvenous defibrillator catheter of claim 40 wherein:
said defibrillator conductor means and said first and second sensing conductors comprise electrically conductive coil windings, each housed in a dielectric sheath.

42. The transvenous defibrillator catheter of claim 41 wherein:
said lumen means includes a single lumen centrally of said catheter body.

43. The transvenous defibrillator catheter of claim 42 wherein:
said electrically conductive coil windings are contained within said central lumen.

44. The transvenous defibrillator catheter of claim 42 wherein:
said defibrillator conductor means are contained within said central lumen, and said first and second sensing conductors comprise a plurality of filaments embedded in said catheter body.

45. The transvenous defibrillator catheter of claim 40 wherein:
said distal sensing electrode is mounted at the distal end of the catheter body and comprises a distal tip electrode.

46. The transvenous defibrillator catheter of claim 45 wherein:
said distal tip electrode includes a platinum alloy wire, and a platinum alloy screen secured with respect to the distal end of said catheter body, for maintaining the wire crumpled and packed against the catheter body.

47. The transvenous defibrillator catheter of claim 46 wherein:
said distal tip electrode is microtexturized.

48. The transvenous defibrillator catheter of claim 45 wherein:
said annular sensing electrode has an outer exposed surface area in the range of from ten to fifty square millimeters.

49. The transvenous defibrillator catheter of claim 40 wherein:
said catheter body is bifurcated to form first and second distal extensions, said first extension including a fixation means for securing the catheter body to endocardial tissue.

50. The transvenous defibrillator catheter of claim 49 wherein:
said defibrillating electrode means is disposed proximally of a junction of the first second distal extensions, and said distal sensing electrode and said annular sensing electrode are mounted on said second distal extension.

51. The transvenous defibrillator catheter of claim 50 wherein:
said distal sensing electrode and said annular sensing electrode are positioned against the septum of the heart when said fixation means secures the catheter body to endocardial tissue.

52. The transvenous defibrillator catheter of claim 40 wherein:
said defibrillating electrode means includes a distal defibrillating electrode mounted to the catheter body at said selected second distance from said annular sensing electrode, and a proximal defibrillating electrode mounted proximally of the distal defibrillating electrode and spaced apart from the distal defibrillating electrode.

53. The transvenous defibrillator catheter of claim 52 wherein:
said defibrillator conductor means includes a first multi-filament conductor connected to said distal defibrillation electrode and a second multi-filament conductor connected to said proximal defibrillation electrode, each of said multi-filament conductors including a plurality of electrically conductive filaments wound about the center of said catheter body in parallel, helical paths.

54. The transvenous defibrillator catheter of claim 53 wherein:
each of the filaments of said defibrillator conductors is embedded in said catheter body substantially over its entire length, and includes an exposed distal portion for electrical coupling with its associated one of said defibrillator electrodes.

55. An intravascular cardioversion system including:
an elongate, flexible and dielectric sensing catheter body having a proximal end region and a distal end region;

a cardiac sensing circuit including a first sensing electrode mounted on said sensing catheter body at said distal end region, a flexible first sensing conductor connected to said first sensing electrode for transmitting electrical pulses between said first sensing electrode and the proximal end region, a second sensing electrode mounted on the sensing catheter body at said distal end region and spaced apart proximally of the first sensing electrode by a predetermined sensing distance, a flexible second conductor connected to the second sensing electrode for transmitting electrical pulses between the second sensing electrode and the proximal end region, and a sensing connector means near said proximal end region for electrically coupling the first and second sensing conductors with a pulse sensing means;

an elongate, flexible and dielectric cardioversion catheter body having a proximal end region and a distal end region; and a cardioversion circuit including a first cardioversion electrode mounted on said cardioversion catheter body near said distal end region, a flexible first cardioversion conductor connected to the first cardioversion electrode for transmitting electrical pulses between the first cardioversion electrode and the proximal end region, a flexible second cardioversion electrode mounted on the cardioversion catheter body proximally of and spaced part from the first cardioversion electrode, a flexible second cardioversion conductor connected to the second cardioversion electrode for transmitting electrical pulses between the second cardioversion electrode and the proximal end region, and a cardioversion connector means near the proximal end region for electrically coupling the first and second cardioversion conductors with a cardioversion pulse generating means; and means for mounting said catheters, with their respective electrodes, in spaced relation ship to each other.

56. The intravascular cardioversion system of claim 55 further including:
a lumen means formed in said sensing catheter body from said proximal end region to said distal end region.

57. The intravascular cardioversion system of claim 55 wherein:
said pulse sensing means and said cardioversion pulse generating means are contained within a body implantable defibrillation unit.

58. An intravascular cardioversion system including:
an elongate, flexible and dielectric sensing catheter body having a proximal end region and a distal end region;
a cardiac sensing circuit including a first sensing electrode mounted on the sensing catheter body at said distal end region, a flexible first sensing conductor connected to the first sensing electrode for transmitting the electrical pulses between the first sensing electrode and the proximal end region, a second sensing electrode mounted on the sensing catheter body at said distal end region and spaced apart proximally of the first sensing electrode by a predetermined sensing distance, a flexible second conductor connected to the second sensing electrode for transmitting electrical pulses between the second sensing electrode and the proximal end region, and a sensing connector means near the proximal end region for electrically coupling the first and second sensing conductors with a cardiac sensing means;

an elongate, flexible and dielectric cardioversion catheter body having a proximal end region and a distal end region;

a cardioversion circuit including a cardioversion pulse generating means, a first cardioversion electrode mounted on said cardioversion catheter body along its distal end region, a flexible first cardioversion conductor mounted to the first cardioversion electrode and contained within the cardioversion catheter body for transmitting electrical pulses between the first cardioversion electrode and the cardioversion pulse generating means, a second cardioversion electrode mounted on the cardioversion catheter body proximally of and spaced apart from the first cardioversion electrode, a flexible second cardioversion conductor connected to the second cardioversion electrode and contained within the cardioversion catheter body for transmitting electrical pules between the second cardioversion electrode and the cardioversion pulse generating means thereby to utilize the first and second cardioversion electrodes as a cardioversion electrode pair, said first and second cardioversion electrodes having surface areas at least three times the surface areas of said first and second sensing electrodes; and means for mounting said catheters, with their respective electrodes, in spaced relationship to each other.

59. The intravascular cardioversion system of claim 58 further including:
a lumen means formed in said sensing catheter body from said proximal end region to said distal end region.

60. The intravascular cardioversion system of claim 58 wherein:
said first and second sensing electrodes have substantially the same surface area.

61. The intravascular cardioversion system of claim 60 wherein:
said first and second cardioversion electrodes have substantially the same surface area.

* * * * *

UNITED STATES PATENT AND TRADEMARK OFFICE
CERTIFICATE OF CORRECTION

PATENT NO. : 5,044,375
DATED : September 3, 1991
INVENTOR(S) : Bach, Jr. et al It is certified that error appears in the above-identified patent and that said Letters Patent is hereby corrected as shown below:

Column 9, Line 63 (Claim 1), the word "pulse" should read as -- pulses --.

Column 11, Line 49 (Claim 21), the word "tap" should read as -- tip --.

Column 15, Line 40 (Claim 55), the word "relation ship" should read as -- relationship --.

Column 16, Line 33 (Claim 58), the word "pules" should read as -- pulses --.

Signed and Sealed this

Twentieth Day of April, 1993

Attest:

MICHAEL K. KIRK

Attesting Officer

Acting Commissioner of Patents and Trademarks